US009044515B2

(12) United States Patent
Baldwin et al.

(10) Patent No.: US 9,044,515 B2
(45) Date of Patent: Jun. 2, 2015

(54) CHEMICAL CONJUGATES FOR TARGETED DEGRADATION UNDER REDUCING CONDITIONS

(75) Inventors: Aaron Baldwin, Orange, CA (US); Kristi Lynn Kiick, Rising Sun, MD (US)

(73) Assignee: UNIVERSITY OF DELAWARE, Newark, DE (US)

( * ) Notice: Subject to any disclaimer, the term of this patent is extended or adjusted under 35 U.S.C. 154(b) by 57 days.

(21) Appl. No.: 13/605,297

(22) Filed: Sep. 6, 2012

(65) Prior Publication Data

US 2013/0244975 A1 Sep. 19, 2013

Related U.S. Application Data (60) Provisional application No. 61/531,416, filed on Sep. 6, 2011.

(51) Int. Cl.
*A61K 47/48* (2006.01)

(52) U.S. Cl.
CPC ..... *A61K 47/48215* (2013.01); *A61K 47/48784* (2013.01)

(58) Field of Classification Search
CPC .......... A61K 47/48215; A61K 47/48784
USPC .............................................. 514/56; 536/21
See application file for complete search history.

(56) References Cited

U.S. PATENT DOCUMENTS

| 7,329,721 | B2 * | 2/2008 | Kozlowski et al. | ........... 528/310 |
| 7,732,427 | B2 | 6/2010 | Kiick et al. | |
| 7,737,131 | B2 | 6/2010 | Kiick et al. | |
| 2010/0297238 | A1 | 11/2010 | Kiick et al. | |
| 2011/0033543 | A1 | 2/2011 | Kiick et al. | |

OTHER PUBLICATIONS

Brinkley M. A Brief Survey of Methods for Preparing Protein Conjugates with Dyes, Haptens, and Cross-Linking Reagents. Bioconjugate Chem 3:2-13, 1992.*
Lutolf et al. Systematic Modulation of Michael-Type Reactivity of Thiols through the Use of Charged Amino Acids. Bioconjugate Chem 12:1051-1056, 2001.*
Gough et al. Aromatic Thiol pK, Effects on the Folding Rate of a Disulfide Containing Protein. Biochemistry 42:11787-11797, 2003.*
Freter et al. Role of the Central Thiol in Determining Rates of the Thiol- Disulfide Interchange Reaction. J Org Chem 44:1771-1774, 1979.*
Hiemstra et al., Rapidly in Situ-Forming Degradable Hydrogels from Dextran Thiols through Michael Addition, Biomacromolecules, (2007), vol. 8, pp. 1548-1556.
Baldwin et al., Tunable Degradation of Maleimide—Thiol Adducts in Reducing Environments, Bioconjugate Chem., (2011), vol. 22, pp. 1946-1953.
Mather et al., Michael Addition Reactions in Macromolecular Design for Emerging Technologies, Prog. Polym. Sci., (2006), vol. 31, pp. 487-531.
Nie et al., Production of Heparin-Functionalized Hydrogels for the Development of Responsive and Controlled Growth Factor Delivery Systems, J. Control Release Oct. 8, 2007, vol. 3, pp. 287-296.

* cited by examiner

*Primary Examiner* — Brandon Fetterolf
*Assistant Examiner* — Yih-Horng Shiao
(74) *Attorney, Agent, or Firm* — RatnerPrestia (57) ABSTRACT

The present invention is related to compositions which can undergo targeted degradation under certain physiological reducing conditions. The compositions may, for example, be hydrogels in which maleimide-functionalized low molecular weight heparin is cross-linked with various thiol-functionalized polyethylene glycol multi-arm star polymers. Both the gelation and degradation of the hydrogels can be modified by careful selection of the thiol. For example, hydrogels prepared from aryl thiol-maleimide adducts can undergo a retro Michael addition-type reaction, leading to degradation of the composition and release of the bioactive molecule.

17 Claims, 6 Drawing Sheets

CHEMICAL CONJUGATES FOR TARGETED DEGRADATION UNDER REDUCING CONDITIONS

CROSS-REFERENCE TO RELATED APPLICATIONS

This application claims priority to U.S. provisional patent application No. 61/531,416, filed Sep. 6, 2011, the content of which is incorporated herein by reference in its entirety for all purposes.

STATEMENT REGARDING FEDERALLY SPONSORED RESEARCH

Research leading to the disclosed invention was funded with funds from the National Institutes of Health under Grant No. 5-P20-RR016472-10 and the National Science Foundation under Grant No. DGE-0221651. Accordingly, the United States government has certain rights in the invention described herein.

FIELD OF THE INVENTION

The invention relates to compositions capable of undergoing targeted degradation under reducing conditions to release bioactive molecules.

BACKGROUND OF THE INVENTION

Hydrogels have been adopted as tools for the study of many diverse types of biological phenomena and in applications such as tissue engineering, biological sensors and microarrays, protein and polymer purification, and drug delivery. They are composed mostly of water and maintain their self-supporting and elastic nature by a network of hydrophilic polymers that are chemically, physically, and/or ionically cross-linked, leading to a material that swells in the presence of water and that can yield mechanical and/or chemical properties similar to those of biological tissues. Polymers of synthetic and natural origins have been exploited for the above applications including poly(ethylene glycol) (PEG), poly(vinyl alcohol), poly(N-isopropylacrylamide), gelatin, collagen, and alginate, and hyaluronic acid, with the application dictating the structural requirement of the chosen polymer.

Heparin, a highly sulfated and variable glycosaminoglycan, is a well-known biomolecule and widely employed anticoagulant in subcutaneous and intravenous therapies, although currently not in a long-term hydrogel delivery format. The anionic character of heparin mediates binding to numerous proteins which in turn mediates many cell fate processes including cell proliferation, differentiation and control of chemokine signaling.

In hydrogels developed for drug delivery, one mode of degradation or release can rely on the reduction of disulfide bonds by glutathione (GSH), a reducing agent found naturally in circulation and cellular compartments. Typically, the extracellular concentration of GSH is relatively low in plasma (ca. 1-20 µM) and relatively high in cells (ca. 0.5-10 mM), providing a level of stability for conjugates and hydrogels outside the cell and aiding in rapid degradation of disulfides intracellularly.

The ability to control degradation in heparin-containing polymeric hydrogels based on PEG, hyaluronic acid, or other polymeric matrices as drug delivery platforms, tissue engineering scaffolds, and related polymeric materials has potential for programmed temporal, spatial, and targeted control of degradation for in vitro cellular studies and future clinical application. Therefore, the development of compositions which permit tunable control over degradation in vivo so as to release a drug or other bioactive molecule according to a particular desired profile or in response to particular physiological conditions would therefore be of great interest.

SUMMARY OF THE INVENTION

One aspect of the invention is directed to a composition comprising a bioactive molecule and a second component (e.g., a polymer, for example a hydrophilic polymer such as polyethylene glycol), wherein the bioactive molecule and the second component are linked by one or more linking units comprising a thioether structural unit obtained by Michael-type addition of a thiol to an $\alpha,\beta$-unsaturated carbonyl group (e.g., a maleimide group) and wherein the thiol has a pKa of less than 9. The composition thus may be considered to be a chemical conjugate of the bioactive molecule and the second component. The thiol and the $\alpha,\beta$-unsaturated carbonyl group are each selected such the thioether structural unit thereby obtained is capable of undergoing a retro Michael-type addition reaction, as will be explained in more detail subsequently. In one embodiment, the bioactive molecule is functionalized with one or more $\alpha,\beta$-unsaturated carbonyl groups and the second component is functionalized with one or more thiol groups, which react in a Michael-type addition to form the composition. In another embodiment, the bioactive molecule initially contains one or more thiol functional groups and the second component initially contains one or more $\alpha,\beta$-unsaturated carbonyl groups, with the bioactive molecule and second component being linked together by reaction of these functional groups to provide the composition through formation of thioether-containing linking units.

The invention is also directed to a method for synthesizing a composition, comprising reacting a functionalized bioactive molecule and a functionalized second component wherein the functionalized bioactive molecule is functionalized with one or more thiol groups having a pKa of less than 9 and/or one or more functional groups capable of acting as a Michael-type acceptor upon reaction with a thiol group and the functionalized second component is functionalized with one or more thiol groups having a pKa of less than 9 and/or one or more functional groups capable of acting as a Michael-type acceptor upon reaction with a thiol group. For example, the method may involve reacting a bioactive molecule functionalized with one or more functional groups capable of acting as a Michael-type acceptor upon reaction with a thiol group (e.g., the functional groups may be $\alpha,\beta$-unsaturated carbonyl groups such as maleimide, provided the resulting thioether is capable of undergoing a retro Michael-type addition reaction) with a second component functionalized with one or more thiol groups having a pKa of less than 9, such as an aryl thiol group. As another example, the method may involve reacting a bioactive molecule functionalized with one or more thiol groups having a pKa of less than 9 (e.g., an aryl thiol group) with a second component functionalized with one or more groups capable of acting as a Michael-type acceptor upon reaction with a thiol group (e.g., a maleimide group).

The invention is also directed to a method of delivering a bioactive molecule to a site within a subject (e.g., a cell) where one or more endogenous thiols (e.g., glutathione, GSH) or exogenous thiols are present, said method comprising administering to the subject a composition comprising a bioactive molecule and a second component, wherein the bioactive molecule and the second component are linked by one or more linking units comprising a thioether structural unit obtained by Michael-type addition of a thiol to an α,β-unsaturated carbonyl group (e.g., a maleimide group) and wherein the thiol has a pKa of less than 9, wherein the composition undergoes a retro Michael-type addition reaction to regenerate the thiol and the α,β-unsaturated carbonyl group rendering the bioactive molecule permanently liberated from the composition after reaction of the endogenous or exogenous thiols with the α,β-unsaturated carbonyl group at the site, whereby the bioactive molecule provides a therapeutic effect to the subject upon release.

In one embodiment, the present invention describes the degradation of reduction-sensitive PEG-LMWH hydrogels cross-linked by maleimide-thiol chemistries. The chemical crosslinking and degradation of the gels was monitored via $^1$H NMR, oscillatory rheology, and spectrophotometric studies. The gelation kinetics and degradation sensitivity to reducing agents is shown to illustrate the utility of the retro Michael-type addition for temporal control of degradation.

In yet another embodiment, the invention provides a composition comprising a bioactive molecule and a polymer, wherein the polymer comprises a plurality of segments linked by one or more linking units comprising a thioether structural unit obtained by Michael-type addition of a thiol to an α,β-unsaturated carbonyl group and wherein the thiol has a pKa of less than 9. The bioactive molecule may be covalently bound to the polymer (e.g., through other such linking units comprising a thioether structural unit) or encapsulated by the polymer.

Figure 4:
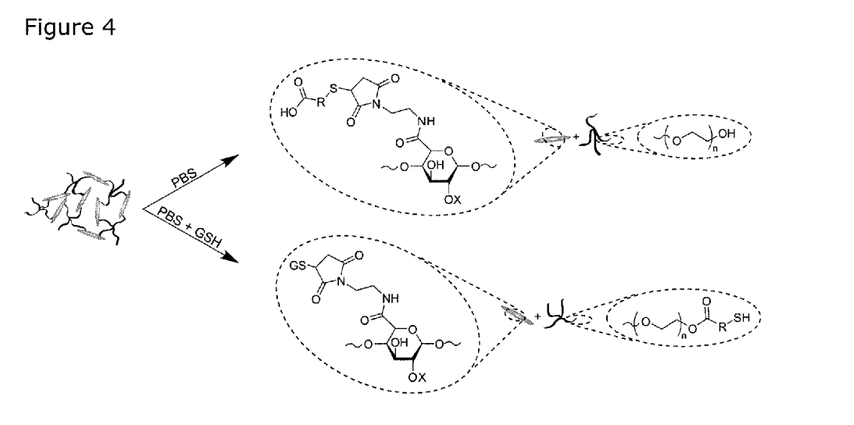
FIG. 4 is a depiction of possible degradation mechanisms for ester and succinimide thioether groups in the hydrogel of FIG. 3.

Referring to FIG. 4, mixtures of both hydrolysis and retro-Michael-type addition products are possible for these hydrogels as a result of degradation.

Figure 5:
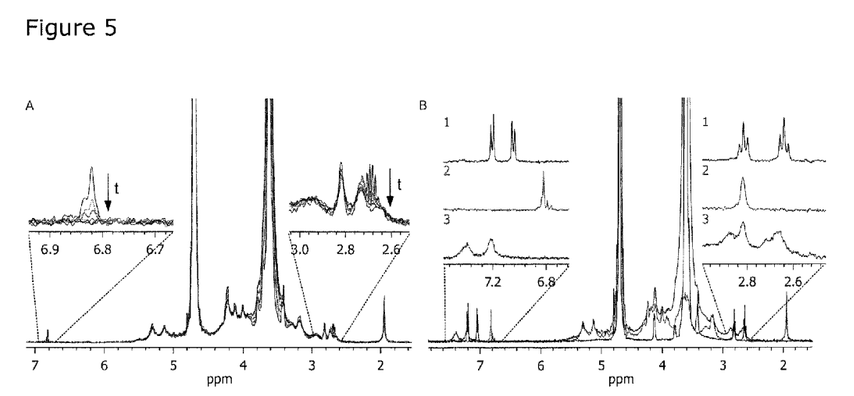
FIG. 5 depicts a $^1$H-NMR spectral analysis of the formation of (A) PEG-MP- and (B) PEG-MPP-containing PEG-LMWH hydrogels.

Referring to FIG. 5, the maleimide peak (6.82 ppm) disappeared within 1 hour for PEG-MP (the arrow indicates increasing time) and in less than 10 minutes for PEG-MPP containing hydrogels. The fast gelation kinetics of PEG-MPP prevented the analysis of the disappearance of the maleimide peak, for reference trace 1=PEG-MPP starting material, 2=Mal-LMWH starting material, 3=final hydrogel showing no resonances from the maleimide protons and broad resonances from the aryl thiol and methylene protons.

Figure 6:
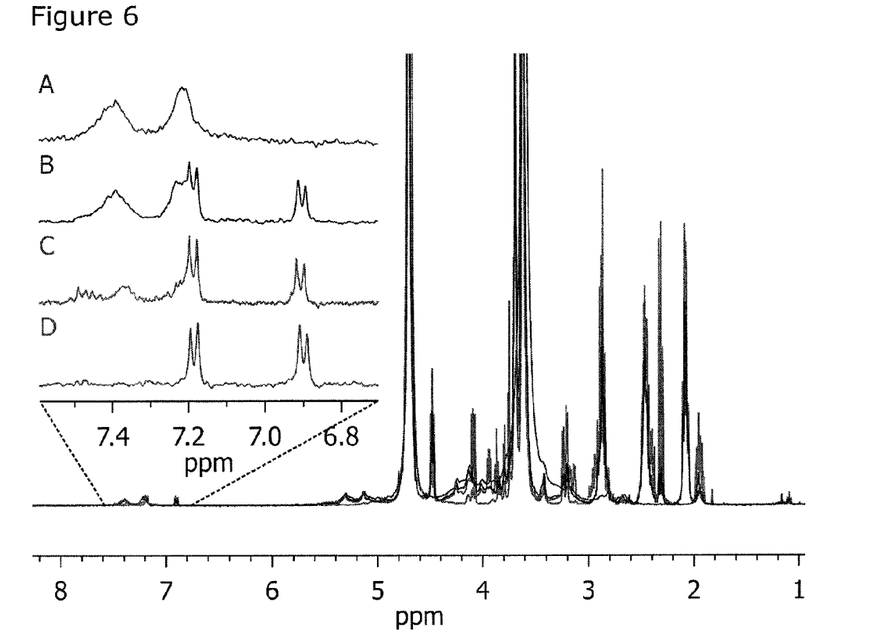
FIG. 6 is a $^1$H-NMR spectrum showing degradation of PEG-MPP-containing PEG-LMWH hydrogels.

Referring to FIG. 6, trace A is the starting hydrogel. Trace B is when the hydrogel is no longer visibly apparent. Trace C is a later time point showing almost complete regeneration of the thiol. Trace D is the starting four-arm PEG-MPP for reference.

Figure 7A:
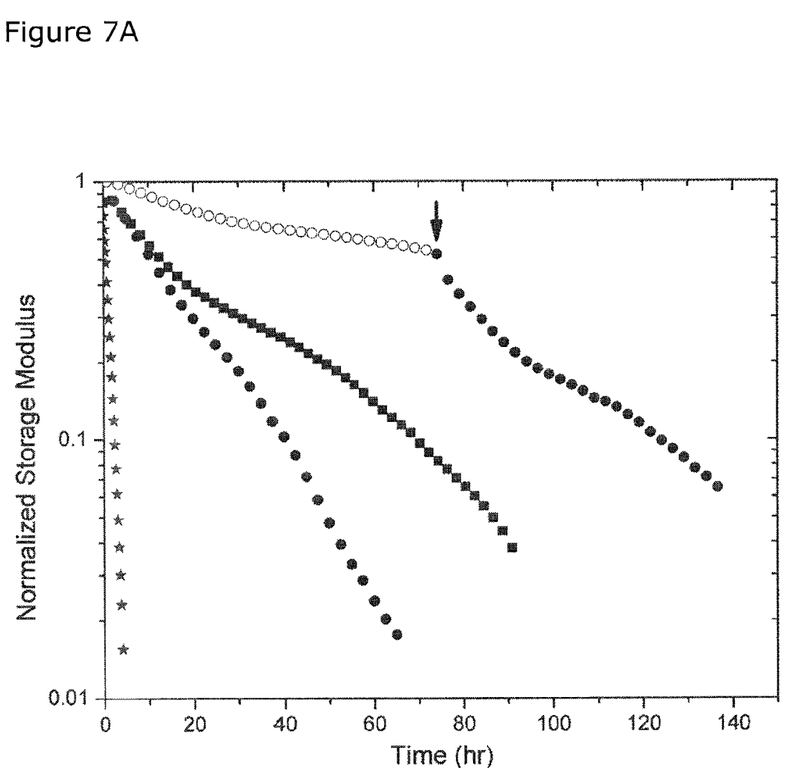
FIG. 7A shows comparison of storage moduli for select degrading hydrogels.

Referring to FIG. 7A, Comparison of storage moduli for select degrading hydrogels: PEG-SH hydrogel (★) LMWH-PEG-MPP (●) and -DMMPP (■) under high reducing conditions (10 mM GSH) and LMWH-PEG-MPP (□) under standard reducing conditions (10 μM GSH). At 72 hrs (arrow) the buffer of the standard reducing condition hydrogel was exchanged for high reducing buffer, showing an increase in rate of degradation.

Figure 7B:
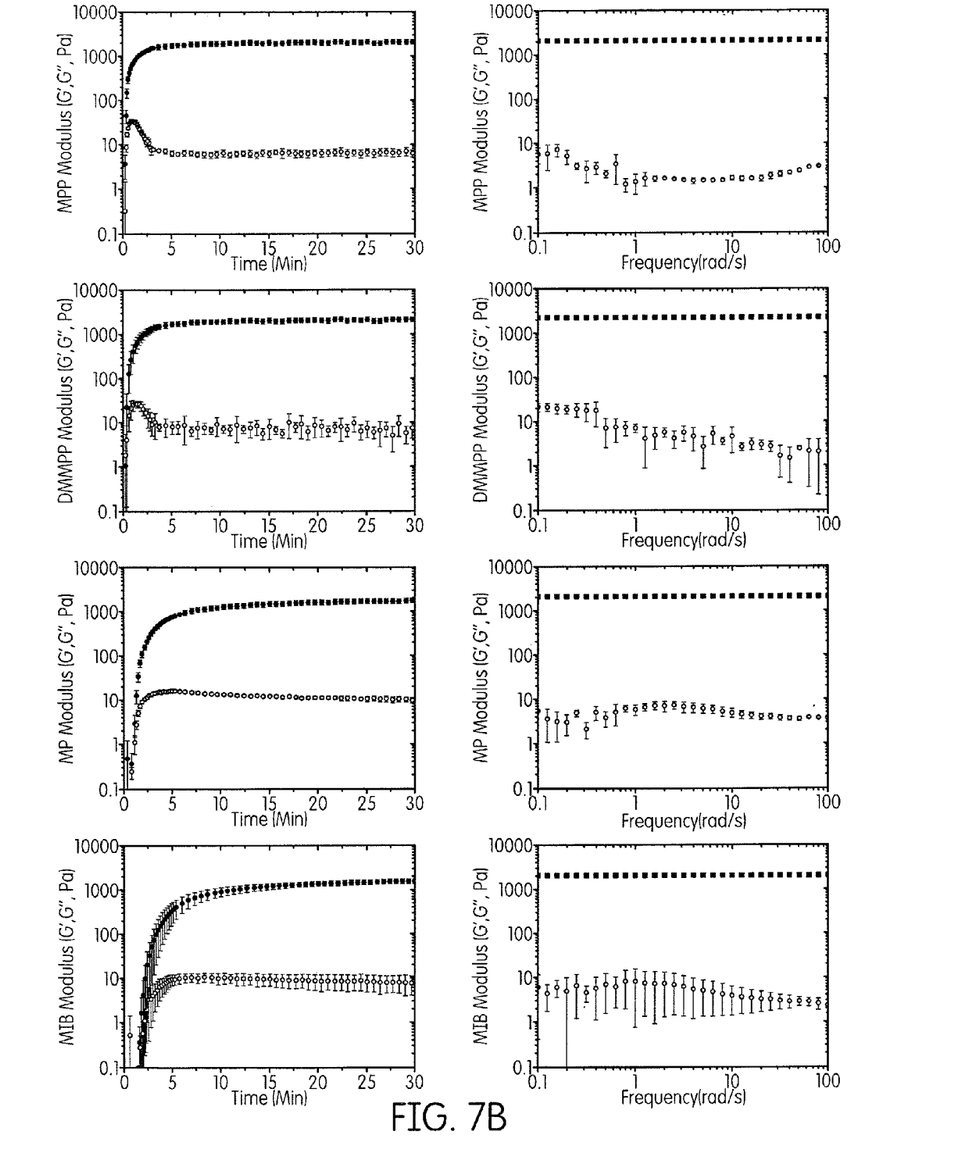
FIG. 7B shows time-sweep and frequency-sweep plots for PEG-LMWH hydrogels for all PEG-thiol functionalities.

Referring to FIG. 7B, Row: 1) PEG-MPP; 2) PEG-DMMPP; 3) PEG-MP; 4) PEG-MIB. Closed symbols indicate G' while open symbols indicate G". Error bars represent the standard deviation of the results of three separate runs. All hydrogels are highly elastic with G'>>G".

Figure 8:
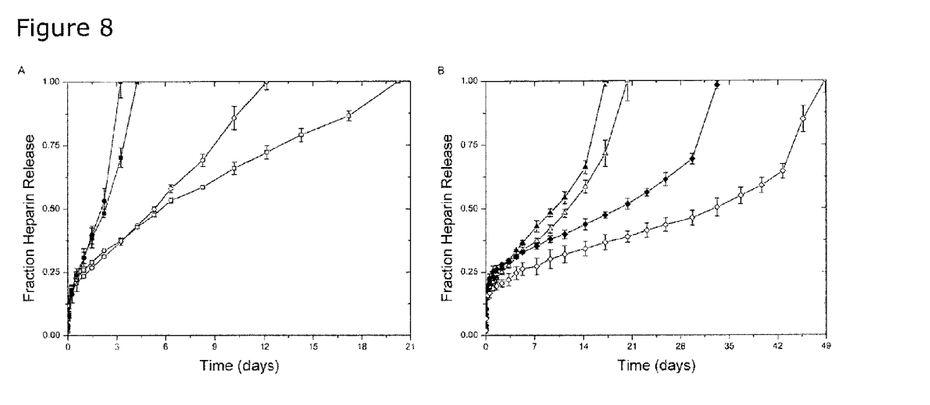
FIG. 8 shows data results from metachromatic dye measurements showing the release rate of LMWH from hydrogels obtained using PEG-MPP, PEG-DMPP, PEG-MP or PEG-MIB.

FIG. 8 shows the release of LMWH from (A) PEG-MPP (●) PEG-DMMPP (■) and (B) PEG-MP (▲) and PEG-MIB (♦) containing hydrogels under standard reducing conditions (10 μM GSH, open) and high reductant load (10 mM GSH, closed).

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

One aspect of the present invention relates generally to a composition comprising a bioactive molecule and a second component, wherein the bioactive molecule and the second component are linked by one or more linking units comprising a thioether structural unit obtained by Michael-type addition of a thiol (containing the functional group —SH) to an α,β-unsaturated carbonyl group. In various embodiments of the invention, the thiol has a pKa of 9 or less, 8 or less, 7 or less or 6 or less. The thiol may, for example, have a pKa of from 6 to 7. Utilizing a thiol having a relatively low pKa value (e.g., 7 or less) has been found to be important in obtaining a composition capable of undergoing a retro Michael-type addition reaction at a practically significant rate when the composition is placed in a physiological environment such as may be found within a cell. The thiol may advantageously be an aryl thiol, wherein a thiol functional group is substituted on an aromatic ring, which may be substituted with one or more other substituents. The aromatic ring may contain one or more heteroatoms such as nitrogen (e.g., the aromatic ring may be a thiazole, pyrimidine or pyridine ring). In this embodiment, the thiol contains an aromatic group (such as a phenyl, thiazole, or pyrimidine group) covalently bound to a sulfur atom, which in turn is covalently bound to the β carbon of the α,β-unsaturated carbonyl group. In another embodiment, the thiol contains a carbon atom that is bound to both the carbon atom of a carbonyl group (such as is found in a carboxylic acid, ester or amide group) and the sulfur atom of the thiol group. For example, the thiol may contain the moiety —C(Y)—S—H, wherein Y is a carboxylic acid (—CO$_2$H), ester (—CO$_2$R) or amide group (e.g., —C(=O)NR$_2$).

In one embodiment, both the α and the β carbon of the α,β-unsaturated carbonyl group are substituted with a carbonyl group (e.g., the α,β-unsaturated carbonyl group may contain the moiety —C(=O)—C=C—C(=O)—). The α,β-unsaturated carbonyl group may be, for example, a maleimide group or any other such group capable of functioning as a Michael-type acceptor in a reaction with a thiol as a Michael-type donor, wherein the S atom of the thiol becomes covalently bound to the β carbon of the α,β-unsaturated carbonyl group, provided the resulting thioether structural unit is capable of undergoing a retro reaction to generate the starting thiol and α,β-unsaturated carbonyl group.

In a further embodiment of the present invention, the thioether structural unit has the structural formula -A-S—R—, wherein A is an aryl moiety (such as a phenyl group), a heteroaromatic moeity (such as a pyrimidine, pyridine or thiazole group), or an organic moiety where the carbon to which the S is bound is also bound to a carbonyl-containing group such as a carboxylic acid, carboxylic ester or amide group and R is a succinimide moiety, with S being covalently bound to a carbon atom of the succinimide moiety. Moiety A may, for example, be a substituted or unsubstituted phenyl, naphthyl or other aromatic ring (including a heteroatom-containing aromatic ring), wherein one or more hydrogens on the aromatic ring may be substituted with alkyl, halo, cyano, nitro or other functional groups. The substituents, and their position, on the aromatic ring may be varied and selected as may be desired in order to control or adjust the nucleophilicity, pKa and other characteristics of the thiol from which the structural unit -A-S— is derived as well as the propensity of the thioether structural unit to undergo a retro Michael-type addition reaction.

In one embodiment of the present invention, the linkages between the bioactive molecule and the second component have the structural formula —$R^5$—$R^1$—S—R—$R^2$—$R^3$— where R is a succinimide moiety, $R^1$ and $R^2$ are each independently an organic moiety such as a substituted or unsubstituted hydrocarbyl moiety (e.g., a C2-C16 hydrocarbyl moiety) and $R^3$ and $R^5$ are each independently a functional group such as an ester, amide, amine or other group covalently bound to the bioactive molecule or polymer, with R being covalently bound to $R^2$ through a nitrogen atom of the succinimide moiety, S being covalently bound to R through a carbon atom of the succinimide moiety, and $R^1$ having an aryl or heteroatom-containing aromatic ring moiety or a carbonyl-substituted alkyl moiety covalently bound to S. $R^5$, in one embodiment, is a carboxylate group —O—C(=O)— wherein the oxygen atom O is covalently bound to the second component or bioactive molecule. The carboxylate group —O—C(=O)— may, for example, be an ester linkage, thereby providing another site within the composition which makes the composition susceptible to degradation (e.g., by hydrolysis of the ester linkage). In another embodiment, $R^1$ contains a carbonyl group (e.g., a carboxylic acid group —$CO_2H$, ester group —$CO_2R$, or amide group, e.g., —C(=O)$NR_2$) covalently bound through the carbon atom of the carbonyl group to the same carbon atom as S.

For example, suitable $R^1$ moieties according to this invention include, but are not limited to, —$CH_2$—$CH_2$—$C_6H_4$—, —C($CH_3$)$_2$—$CH_2$—$C_6H_4$—, and —$CH_2$—$C_6H_4$—, wherein the moiety —$C_6H_4$— is covalently bound to S. Additional suitable $R^1$ moieties include —$CH_2$-T-, and —(CH$_2$)$_4$—Py—, where T is a thiazole moiety and Py is a pyrimidine moiety with T or Py being covalently bound to S. $R^1$ may, for example, also be —(CH$_2$)$_n$—CH(CO$_2$R$^6$)—, wherein n is an integer of from 1 to 10 and $R^6$ is H, an organic moiety (e.g., a C1-C16 hydrocarbyl group), a bioactive molecule, or a second component.

Suitable functional groups $R^3$ and $R^5$ include, but are not limited to, amino, amido, ester, alkenyl, triazole, ether, urethane, urea and thio functional groups. Functional groups $R^3$ and $R^5$ may be formed using any suitable chemistry, such as the reaction of an amine with a carboxylic acid to form an amide functional group, the reaction of an alcohol with a carboxylic acid to form an ester functional group, the reaction of an amine with an acrylate to provide a Michael-type adduct, the reaction of an alkyne and an azide to form a triazole, a Diels Alder reaction, the reaction of a tetrazine and a cyclooctene, the reaction of an isocyanate group and an active hydrogen-containing group such as an amino or hydroxyl group to form a urethane or urea group, the Michael-type addition reaction of a thiol and an α,β-unsaturated carbonyl group, and the like.

A further embodiment of the present invention comprises a low molecular weight heparin (LMWH) and hydrophilic multi-arm star polymer incorporated into a hydrogel matrix, wherein the low molecular weight heparin is functionalized with a maleimide and the hydrophilic polymer is a thiolated four-arm star polyethylene glycol. This composition may be obtained by reacting a maleimide-functionalized heparin with a thiolated four-arm star PEG wherein the thiol functional groups have a pKa of less than 9.

Yet another embodiment of the present invention is a method of delivering one or more of the aforementioned compositions to a site within a subject where one or more endogenous thiols are present or at which an exogenous thiol could be liberated or added, wherein the composition undergoes a retro Michael-type addition to regenerate the thiol and α,β-unsaturated carbonyl group. The bioactive molecule released from the composition by the retro Michael-type addition reaction, with release permitted by the retro Michael-type addition reaction and subsequent thiol exchange, provides a therapeutic effect to the subject.

Previously, thiol-maleimide Michael-type addition reactions have been used to make hydrogels employing a variety of compositions. However, it has not been previously reported that hydrogels made using thiol-maleimide chemistry may be modified, through selection of the type of thiol used, to be capable of undergoing retro Michael-type addition reactions leading to degradation of the hydrogel. It has now been discovered that the use of highly nucleophilic thiols such as aryl thiols in the preparation of bioactive molecule-containing compositions such as hydrogels may, under physiological conditions, undergo a retro Michael-type addition at sufficiently high rate to generate free α,β-unsaturated carbonyl (e.g., maleimide) functional groups. The free maleimide groups, which could be present on the bioactive molecule or the second component, then react with endogenous or exogenous thiols such as glutathione. This results in selective degradation of the composition because the thiol generated from the retro Michael-type reaction cannot re-react with the released maleimide group once the released maleimide group has reacted with the endogenous or exogenous thiols. Degradation of the composition leads to release of the bioactive molecule from the composition, wherein the released bioactive molecule becomes available to provide a therapeutic effect. Applications for compositions according to this invention include, but are not limited to, drug release from gels, gel degradation, drug release from soluble polymer-drug conjugates, control of cell phenotype by temporal degradation of gels, and cancer-specific drug delivery.

In one embodiment, the composition is a hydrogel, i.e., a material that swells in water. In another embodiment, the composition is soluble in water. In still another embodiment, the composition is neither soluble in water or swellable in water. The water solubility/swelling characteristics of the composition may be varied as may be desired by selecting and controlling variables such as the molecular weight, chemical composition and structure of the second component as well as the extent of linking between the second component and the bioactive molecule, among other factors. For example, a more highly crosslinked composition will generally tend to provide a hydrogel, while a composition where only a single linkage between the second component and the bioactive molecule exists may be water-soluble.

More than one bioactive molecule may be linked to a single second component molecule. The second component may be linked to more than one type of bioactive molecule. More than one type of second component may be present in the composition. The composition may comprise a plurality of second component molecules (which may be the same as or different from each other) and a plurality of bioactive molecules (which may be the same as or different from each other), which may be multiply linked together to form a crosslinked matrix.

As previously mentioned, one embodiment of the invention provides a composition comprising a bioactive molecule and a polymer, wherein the polymer comprises a plurality of segments linked by one or more linking units comprising a thioether structural unit obtained by Michael-type addition of a thiol to an $\alpha,\beta$-unsaturated carbonyl group and wherein the thiol has a pKa of less than 9. A portion of the backbone of a linear polymer of this type may, for example, be generally represented as —X-Seg-X-Seg-X-Seg-, wherein X is a linking unit comprising a thioether structural unit and Seg is a segment. The bioactive molecule may be covalently bound to the polymer (e.g., through other such linking units comprising a thioether structural unit) or physically encapsulated by the polymer. The segments of the polymer may be the same as or different from each other. For example, one or more segments may be hydrophilic and one or more segments may be hydrophobic (e.g., the polymer may be a block copolymer containing one or more blocks derived from one or more hydrophilic monomers and one or more blocks derived from one or more hydrophobic monomers). The polymer may be prepared, for example, by reacting a first segment functionalized with one or more thiol groups having a pKa of 9 or less (e.g., an aryl thiol functional group) with a second segment functionalized with one or more $\alpha,\beta$-unsaturated carbonyl groups such as maleimide groups. The individual segments may be monomeric, oligomeric or polymeric. Any of the linking chemistries previously described may be utilized in this embodiment of the invention as well.

Yet another embodiment of the present invention is a method of delivering one or more of the aforementioned compositions to a site within a subject where one or more endogenous thiols are present or at which an exogenous thiol could be liberated or added, wherein the second component of the composition (e.g., a polymer comprised of multiple thioether-linked segments) undergoes a retro Michael-type addition such that the second component at least partially degrades to discrete segments. The initially encapsulated or bound bioactive molecule released from the composition by the retro Michael-type addition reaction and subsequent thiol exchange provides a therapeutic effect to the subject.

Bioactive Molecule

Bioactive molecules according to this invention include, but are not limited to, polysaccharides (including oligosaccharides), growth factors, cytokines, peptides, peptide-modified polymers (polymers covalently modified with peptide), proteins, polysaccharide-modified polymers (polymer covalently modified with polysaccharide), peptoids, peptoid-modified polymers (polymers covalently modified with peptoid), and small-molecule drugs. A bioactive molecule is defined herein to mean a biologically active agent, i.e., any compound or substance that has an effect on a biological system such as living tissue or living cells.

One particularly interesting bioactive molecule is heparin, which is a highly sulfated glycosaminoglycan with a high negative charge that gives rise to interactions with many proteins such as growth factors (such as fibroblast growth factor (FGF), vascular endothelial growth factor (VEGF)), coagulation factors (antithrombin III), chemokines (PF-4), pathogen proteins (HIV-1 gp120, Tat), and adhesion proteins (selectins, fibronectin). Heparin formulations have a long history of clinical use as anticoagulants. Unfractionated and low molecular weight heparin (LMWH) are standard treatments for myocardial infarction, cardiovascular surgery, coronary angioplasty, coronary stents, and numerous other conditions. LMWH, which can be delivered subcutaneously, offers advantages over unfractionated heparins, which require IV delivery, such as reduced risk of hemorrhage, improved clearance rates, and more predictable pharmacokinetics. Perhaps most importantly, subcutaneous injection of LMWH can safely be administered at home without the need to monitor activated partial-thromboplastin time that is necessary with unfractionated heparin.

There has been significant effort to develop oral formulations for heparin delivery, owing to compliance issues with subcutaneous injections in outpatient populations. Unfortunately, oral delivery approaches are hampered by the fact that heparin is not readily or consistently absorbed by the gastrointestinal tract, thus injection remains the primary route of administration. Additionally, compliance with daily injections regimens is a serious problem; in one study, lack of compliance resulted in uncertain prophylaxis in 28% of adults and 100% of patients under 20 years of age. Accordingly, both oral and recurrent subcutaneous delivery modalities have drawbacks in the maintenance of consistent drug concentrations within therapeutic ranges, which is a critical difficulty for disease prevention. The development of time-released heparin formulations would represent a significant improvement in anticoagulation therapies, especially in pediatric patients.

The bioactive molecule may already contain one or more functional groups capable of forming a chemical linkage to the second component through a Michael-type addition reaction to provide a composition in accordance with the invention or may be modified to provide such functional groups. The functional group may be a thiol or an $\alpha,\beta$-unsaturated carbonyl group such as a maleimide group, depending upon the reactive functional group(s) present in the second component to be incorporated into the composition. For example, if the second component contains one or more aryl thiol functional groups, the functional group on the bioactive molecule may be a maleimide group capable of undergoing a Michael-type addition reaction with the aryl thiol to provide the composition (i.e., a chemical conjugate of the bioactive molecule and the second component, which are linked by at least one linking unit comprising a thioether structural unit, the thioether being capable of undergoing a retro Michael-type addition reaction).

In one embodiment of the invention, the bioactive molecule contains one or more carboxyl groups (e.g., —C(=O)O⁻ or —C(=O)—OH) which are reacted with the amine group of an amino-functionalized maleimide (e.g., $R^4$—$R^2$—$NH_2$, where $R^4$ is a maleimide moiety covalently bound to $R^2$ through the nitrogen of the maleimide ring and $R^2$ is a divalent organic moiety such as a C2-C16 hydrocarbyl group, e.g., —CH$_2$—CH$_2$—) to form an amide linkage to the bioactive molecule and to provide the bioactive molecule with a pendant maleimide group (i.e., the bioactive molecule is functionalized with one or more maleimide groups).

Second Component

The second component to be linked to the bioactive molecule or molecules may be of any suitable composition or structure which imparts the desired characteristics and properties to the chemical conjugate composition formed by linkage of the second component and the bioactive molecule(s). For example, the second component may be water-soluble, water-insoluble or water-swellable, may be a small molecule (monomeric) or polymeric (including oligomeric), may be of low or high molecular weight, and/or may be biologically active or biologically inactive. In one embodiment, the second component is a bioactive molecule, which may be the same as or different from the bioactive molecule(s) to be linked to the second component. A polymer may be utilized as the second component of the invention, as described in more detail below.

Polymers

Polymers suitable for use in this invention can be hydrophilic, hydrophobic or hydrophilic-hydrophobic amphiphilic polymers (or block polymers). The polymer may be of natural or synthetic origin. As used herein, the term "polymer" includes not only compounds containing repeating units of one or more monomers but also macromolecular compounds which do not contain such repeating units.

Hydrophilic polymers according to this invention include, but are not limited to, polyalkylene glycols, poly(vinyl alcohols), poly(acrylamides), poly(acrylates), poly(acrylic acids), poly(methacrylic acids), heparins, gelatins, collagens, alginates and hyaluronic acids. The hydrophilic polymer may be water-soluble and may be linear or branched.

For drug delivery and biological applications, the following hydrophilic polymers are particularly suitable: poly(vinyl alcohols), polyethylene-vinyl acetates, poly(enol-ketones), poly(meth)acrylic acids, polyhydroxyalkyl(meth)acrylates, poly(acrylamides), poly(N-alkyl acrylamides), copolymers of one or more alkyl(meth)acrylates with one or more monomers selected from the group consisting of hydroxyalkyl (meth)acrylates, (meth)acrylic acids and acrylamides, polyalkylene glycols such as polyethylene glycols and co-polyols of ethylene oxide and propylene oxide, polyethylene oxides, poly(glycolic acid), poly(lactic acid), poly(lactic-co-glycolic acid), poly(caprolactone), poly(3-hydroxybutyrate), poly (ortho esters), poly(anhydrides), poly(amido amines), poly (urethanes), and poly(phosphazenes), among others.

A hydrophilic polymer particularly suitable for use in this invention is poly(ethylene glycol), which is also referred to as PEG. PEG is a linear or branched neutral polyether with the chemical formula in linear, unfunctionalized form being HO—(CH$_2$CH$_2$O)$_n$—H, with n typically being from about 3 to about 500. PEG is highly soluble in water and many organic solvents (e.g., methylene chloride, ethanol, toluene, acetone, and chloroform), and is readily available in various sizes and functionalized architectures (e.g., amino-, carboxyl-, and sulfhydryl-terminated). Lower molecular weight PEGs are viscous and colorless liquids, whereas higher molecular weight PEGs are waxy solids whose melting points are proportional to their molecular weights with h an upper limit near 67° C. In one embodiment, the PEG is branched and contains three or more branches (e.g., three, four, five, six or more branches).

Hydrophobic polymers according to this invention include, but are not limited to, homopolymers and copolymers of acrylics (e.g., alkyl(meth)acrylates), olefins, styrenes and other vinyl aromatic monomers, vinyl acetals, vinyl chlorides, vinylidene chlorides, vinyl esters, vinyl ethers, vinyl ketones, vinylpyridine, and vinylpyrrolidone.

Hydrophilic-hydrophobic amphiphilic polymers (or block polymers) useful in the invention include polymers which contain, within the same polymer chain, at least one hydrophilic block (such as a segment obtained by polymerization of one or more hydrophilic monomers such as an alkylene oxide, hydroxyalkyl(meth)acrylate or (meth)acrylic acid) and at least one hydrophobic block (such as a segment obtained by polymerization of one or more hydrophobic monomers such as an olefin, vinyl aromatic monomer, or vinyl chloride). Illustrate examples of such block copolymers include, but are not limited to, poly(styrene-block-hydroxyalkyl(meth)acrylate)s, poly(styrene-block-(meth)acrylic acid)s, poly(styrene-block-ethylene oxide)s, poly(ethylene oxide-block-propylene oxide)s and the like.

Other types of polymers suitable for use in the present invention include, but are not limited to, proteins and polypeptides.

The second component (e.g., polymer) may already contain one or more functional groups capable of forming a thioether-containing linkage to the bioactive molecule to provide a composition in accordance with the invention or may be modified to provide such functional groups. Where the second component is a polymer, such functional groups may be present at the terminal positions of some or all of the ends or branches of the polymer and/or positioned along or pendant to the polymer backbone. The functional group may be a thiol or an α,β-unsaturated carbonyl group such as a maleimide group, depending upon the reactive functional groups present in the bioactive molecule component to be incorporated into the composition. For example, if the bioactive molecule contains one or more α,β-unsaturated carbonyl functional groups, the functional group on the second component (e.g., polymer) may be an aryl thiol group (—Ar—SH) capable of undergoing a Michael-type addition reaction with the α,β-unsaturated carbonyl functional groups to provide the composition, which is capable of undergoing retro Michael-type addition to again generate the thiol.

In one embodiment of the invention, the second component (e.g., polymer) contains one or more hydroxyl groups which are reacted with the carboxylic acid group of a mercaptoacid (a thiol-functionalized carboxylic acid, having, for example, the structural formula H—O—C(=O)—R$^4$—S—H where R$^4$ is, for example, an aryl or aralkyl moiety having an aryl group covalently bound to S) to form an ester linkage. R$^4$ may contain 6 to 16 carbon atoms or more, with the aromatic ring of the aryl group being substituted or unsubstituted. R$^4$ may also be a moiety containing a heteroaromatic ring such as a thiazole, pyridine or pyrimidine ring, with the heteroaromatic ring being substituted or unsubstituted. An alkylene moiety such as —(CH$_2$)$_n$—, where n is from 1 to 10, may be present between the heteroaromatic ring and the carboxylic acid group H—O—C(=O)—.

In another embodiment, the mercaptoacid contains two or more carboxylic acid groups, each of which is capable of reacting with an active hydrogen-containing group (e.g., a hydroxyl group or an amino group) of the second component to form an ester or amide linkage or the like, with one of the carboxylic acid groups being substituted on the same carbon atom as the thiol group. Examples of such mercaptoacids include, but are not limited to, 2-mercaptosuccinic acid and 2-mercaptoadipic acid.

The mercaptoacid is selected such that the pKa of the thiol groups in the resulting thiolated second component is 9 or less, or 8 or less, or 7 or less, e.g., 6 to 7, in accordance with various aspects of the invention. Suitable mercaptoacids include, but are not limited to, 4-mercaptophenylpropanoic acid, 2,2-dimethyl-3-(4-mercaptophenyl)propionic acid, 4-mercaptophenylacetic acid, 2-(2-mercaptothiazol-5-yl) acetic acid, 2-(2-mercaptothiazol-4-yl)acetic acid, 5-(4-amino-2-mercaptopyrimidin-5-yl)pentanoic acid, 2-mercaptosuccinic acid, 2-mercaptobenzoic acid, 2-(4-mercaptophenyl)acetic acid), and 3-(4-mercaptophenyl) propanoic acid.

Hydrogels

Compositions in accordance with the present invention may be formulated to be hydrogels. Hydrogels have been commonly used for controlled release of drugs in many applications and as substrates for cell growth in regenerative medicine applications. They are composed mostly of water and maintain their self-supporting and elastic nature due to a network of hydrophilic polymers that are chemically, physically, or ionically crosslinked leading to a material that swells to a high degree. Hydrogels may be formulated to have mechanical and/or chemical properties similar to those of biological tissues.

EXAMPLES

The following examples further illustrate but by no means limit the present invention.

Materials:

Four-arm, hydroxyl-functionalized polyethylene glycol (PEG) (Mn 10,000 g mol$^{-1}$) was purchased from JenKem Technology USA Inc. (Allen, Tex., USA). Four-arm, thiol-functionalized PEG (PEG-SH) (Mn 10,000 g mol$^{-1}$) was purchased from Creative PEG Works (Winston Salem, N.C., USA). Mercaptoisobutyric acid (MIB) was purchased from TCI America (Portland, Oreg., USA). 4-Mercaptophenylpropionic acid (MPP) and 2,2-dimethyl-3-(4-mercaptophenyl) propionic acid (DMMPP) were purchased from Toronto Research Chemicals (North York, Ontario, Canada). Nitrous acid depolymerized low molecular weight heparin (LMWH) was purchased from Celsus (Cincinnati, Ohio, USA). N-(2-aminoethyl)maleimide, trifluoroacetate salt (AEM), 1-hydroxybenzotriazole hydrate (HOBT), 2-(N-morpholino) ethanesulfonic acid (MES), 3-mercaptopropionic acid (MP), p-toluenesulfonic acid monohydrate (PTSA), and light mineral oil were purchased from Sigma-Aldrich (St. Louis, Mo., USA). N-(3-dimethylaminopropyl)-N'-ethylcarbodiimide hydrochloride (EDC.HCl), and all other reagents and materials were purchased from Fisher Scientific unless noted (Pittsburgh, Pa., USA). Proton nuclear magnetic resonance ($^1$H-NMR) spectra were acquired under standard quantitative conditions at ambient temperature on a Bruker DRX-400 NMR spectrometer (Billerica, Mass.). The spectra of all purified compounds were recorded in deuterated chloroform (CDCl$_3$) or deuterium oxide (D$_2$O).

The estimated pka and log D (pH 7.4) values of the various mercaptoacids used are shown in the following Table 1.

TABLE 1

| Mercaptoacid | —SH pKa (est.) | logD (pH 7.4)(est.) |
|---|---|---|
| 3-Mercaptopropanoic acid (MP) | 10.4 | −2.6 |
| 3-Mercaptoisobutyric acid (MIB) | 10.8 | −2.1 |
| 4-Mercaptophenylpropanoic acid (MPP) | 6.7 | −1.3 |
| 2,2-Dimethyl-3-(4-mercaptophenyl)propionic acid (DMMPP) | 6.8 | −0.6 |

Figure 1:
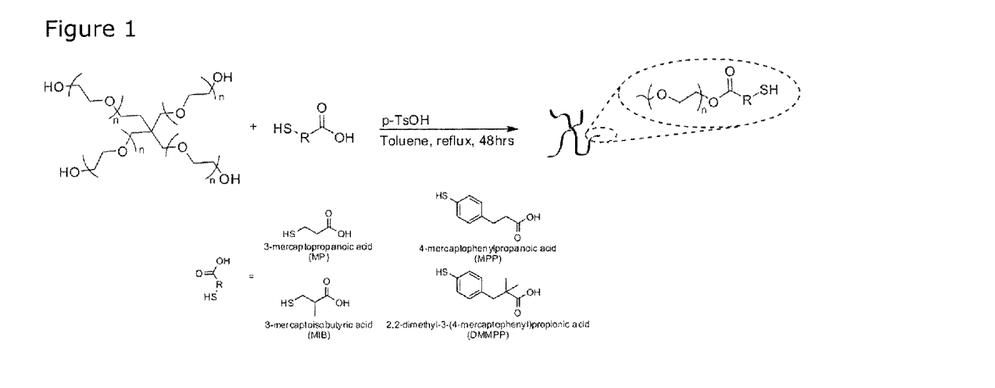
FIG. 1 is a schematic of an exemplary synthesis of a thiol-functionalized (thiolated) four-arm polyethylene glycol (PEG)

Synthesis of PEG-Thiol:

The synthesis of thiolated four-arm PEG (as illustrated in FIG. 1) was performed as previously reported. PEG (1 meq.), mercaptoacid (40 meq. MP, MIB, MPP or DMMPP) and PTSA (0.4 meq.) were dissolved in toluene. Under a flow of nitrogen the reaction was refluxed with stirring for 48 hrs. Water was collected by using a Dean Stark trap. Toluene was removed under reduced pressure and the polymer was precipitated 3 times in cold ether. The polymer was reduced by dissolving 1 meq polymer in methanol with DTT (1 meq.) and triethylamine (1 meq.) under nitrogen for 5 hours. The finished reaction was acidified with trifluoroacetic acid (1.1 meq.), and the polymer was precipitated in ether and rinsed with 2-propanol then hexane. Functionality was determined via $^1$H-NMR spectroscopy and was ~4 (>95%) for all derivatives. All products were stored under argon or vacuum at room temperature to maintain the reduced thiol during storage.

PEG-MPP $^1$H NMR (CDCl$_3$): δ=7.24-7.18 (8H, d), 7.11-7.06 (8H, d), 4.22 (8H, t), 3.90-3.35 (900H, bs), 2.94 (8H, t).

PEG-DMMPP $^1$H NMR (CDCl$_3$): δ=7.22-7.15 (8H, d), 7.05-6.98 (8H, d), 4.21 (8H, t), 3.90-3.35 (900H, bs), 2.81 (8H, s), 1.18 (24H, s).

PEG-MP $^1$H NMR (CDCl$_3$): δ=4.28 (8H, t), 3.90-3.35 (900H, bs), 2.84-2.63 (16H, m), 1.69 (4H, t).

PEG-MIB $^1$H NMR (CDCl$_3$): δ=4.28 (8H, m), 3.90-3.35 (900H, bs), 2.84-2.60 (12H, m), 1.57 (4H, t), 1.31-1.23 (12H, d).

Synthesis of Maleimide-Functionalized LMWH (Mal-LMWH):

The molecular weight of LMWH was characterized by size exclusion chromatography (SEC) using previously described methods. The SEC system comprised a Waters 515 HPLC pump (Milford, Mass., USA), two Waters Ultrahydrogel (7.8×300 mm) columns in series, a Waters 2414 refractive index detector, a Waters 2996 photodiode array detector and a Precision Detectors light scattering unit (Bellingham, Mass., USA). The number average molecular weight was determined to be 8,300 g mol$^{-1}$.

Figure 2:
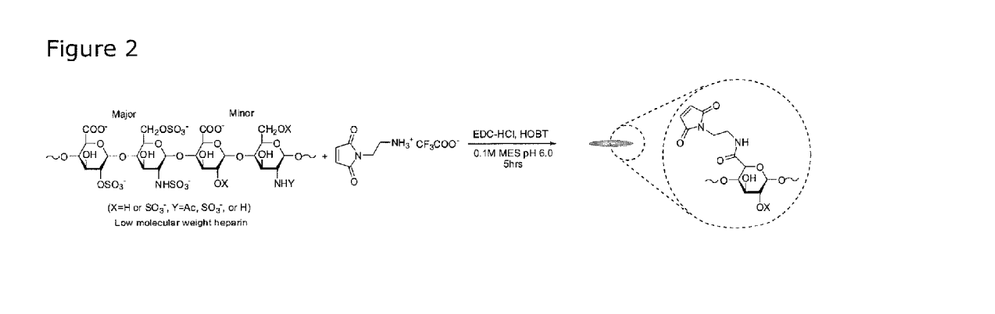
FIG. 2 is a schematic of an exemplary synthesis of a maleimide-functionalized low molecular weight heparin (LMWH)

The synthesis of maleimide-functionalized heparin (as illustrated in FIG. 2) was performed as previously described with slight modification of reactant quantities to control the extent of modification. 500 mg LMWH (0.06 mmol) was dissolved with 103 mg HOBT (0.67 mmol), 103 mg AEM (0.67 mmol) and 103 mg EDC.HCl (0.54 mmol) dissolved in 50 ml of 0.1M MES pH 6.0. The reaction proceeded overnight at room temperature with stirring. The product was purified by dialysis (MWCO 1000) against 4 L of 1M NaCl solution and then subsequently against de-ionized water each with 4 volumes exchanges over 24 hrs. The freeze-dried sample was characterized via $^1$H-NMR indicating a degree of functionalization of 2.6.

MAL-LMWH $^1$H NMR (400 MHz, D$_2$O): δ=6.83 (2H, s), 5.60-5.05 (29H, heparin anomeric proton, bs).

Hydrogel Formation:

Hydrogel formation was accomplished by mixing separate solutions of the functionalized PEG and LMWH, prepared individually in phosphate buffered saline (PBS, 10 mM phosphate and 150 mM NaCl). Hydrogels prepared with alkyl thiol-functionalized PEGs (MP and MIB) were gelled at a pH of 7.0 and an initial temperature of 25° C. Hydrogels prepared with aryl thiol-functionalized PEG were gelled at a pH 6.6 and an initial mixing temperature of 4° C. to slow the gelation and permit mixing before gelation occurred. Reducing the pH and temperature allowed sufficient time to briefly vortex mix and load samples before gelation occurred. Self-supporting hydrogels were formed upon mixing the two solutions. For simplicity of analysis, 5 wt % gels were used in all experiments.

Further, control gels for the oscillatory rheology degradation experiments were crosslinked with disulfide bonds and were formed as previously described. In short, 5.3 wt % PEG-SH was dissolved in 10 mM glycine buffer containing 0.01×(molar ratio to PEG-SH) iron lactate and cysteine.

Hydrogel Formation Analysis by Oscillatory Rheology:

Oscillatory rheology was used to determine the gelation kinetics and final modulus for all four types of LMWH and PEG hydrogels (PEG-MP, PEG-MIB, PEG-MPP, and PEG-DMMPP). Samples were gelled in situ by co-injection of the separately dissolved functionalized polymers onto the rheometer Peltier plate. An AR-2000 rheometer (TA Instruments, New Castle, Del.) was used to measure oscillatory shear properties at 37° C. with maximum shearing amplitude of 1.0%. A 20 mm, 1° 56" cone plate geometry with a 33 μm truncation requiring 40 μL of solution was used in all experiments. Time sweep studies were performed at a constant 6 rad $s^{-1}$ while frequency sweeps were conducted over a logarithmic scale from 0.1 rad $s^{-1}$ to 100 rad $s^{-1}$. The rheometer Peltier plate was chilled to 25° C. for alkyl thiol-functionalized PEG-containing gels, and 4° C. for aryl thiol-functionalized PEG-containing gels, before co-injection of polymers onto the plate. Time sweep data collection, and a 3-minute temperature ramp to 37° C., was initiated once the polymers were injected onto the stage. Light mineral oil was applied to the perimeter of the sample to prevent evaporation over the course of the experiment.

The mixing of the solutions of functional PEG and LMWH resulted in the rapid in situ formation of an elastic hydrogel on the rheometer stage. PEG-MPP was the most rapid hydrogelator. The PEG-MPP hydrogel was formed within seconds of mixing the dissolved components (<6 s). Although the mixed components were added to the rheometer Peltier plate before an increase of viscosity was observed, the first data point recorded at 6 seconds indicated that the storage modulus (G') had increased to 3.8±2.1 Pa, greater than the loss modulus (G'). The reduction in G" with time most likely indicates the initial presence of kinetically trapped, unreacted functionalities between covalent crosslinks that eventually react to form elastic crosslinks as time progresses. This occurrence was observed only for the aryl thiol PEG-containing hydrogels and was absent in alkyl thiol PEG-containing gels, possibly due to fewer kinetically entrapped network defects.

Variations in the rate of gelation were also assessed from the rheology experiments. Gelation occurred within 15 s, 50 s and 90 s for PEG-DMMPP, PEG-MP, and PEG-MIB respectively. The rate of gelation of the hydrogels was related to the Michael donor reactivity of the thiols. The aryl thiol derivatives with lower pKa values relative to the alkyl thiols (e.g., 6.6 vs. 10.3) thus had faster reaction rates. The same dependence on Michael donor reactivity was observed for the final equilibration of the ultimate storage modulus of the hydrogels, with gels achieving 90% of their final modulus in 9 minutes for PEG-MPP, 20 minutes for PEG-DMMPP, 60 minutes for PEG-MP and 70 minutes for PEG-MIB. Regardless of the identity of the mercaptoacid-functionalized PEG, the resulting hydrogels exhibited stable elastic moduli over all frequencies measured (0.1 rad/s to 100 rad/s) with the ratio of G"/G' or tan(δ) being less than 0.01 for all hydrogels over all frequencies.

The ultimate storage modulus measured in the rheology experiments was used to compare the consistency of the elastic storage modulus between the various gels. The measured equilibrium storage moduli for the various gels were all approximately 2.1 kPa (p=0.79), regardless of the identity of the mercaptoacid-functionalized PEG and the corresponding differences in gelation kinetics. The apparently low elastic moduli values, compared to the predicted modulus for these hydrogels from classical rubber elasticity theory (19.1 kPa), is likely due to the formation of non-elastically active chains, such as cycles or loops, arising from the crosslinking of these materials under relatively dilute conditions. Hydrogels prepared at higher polymer concentrations (ca. 10-15 wt %) yielded storage modulus values that were consistent with those predicted from classical rubber elasticity theory. The conservation of modulus across all mercaptoacid-functionalized PEG containing PEG-LMWH hydrogels indicates that the gelation of these hydrogels is not affected, over the timescales of network formation, by other factors such as disulfide bond formation or ring-opening of the maleimide. Therefore, direct comparisons of the degradation kinetics of the gels are possible.

Figure 3:
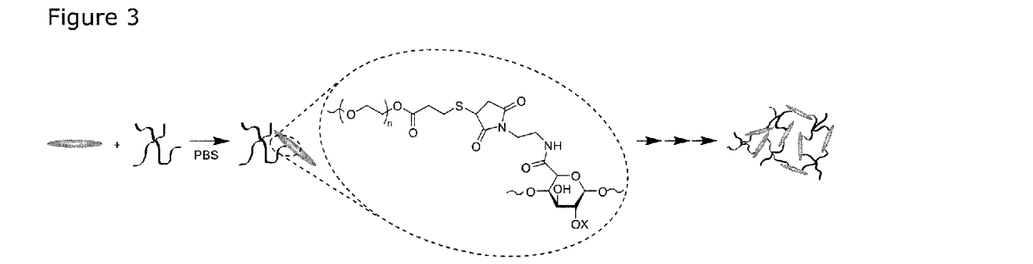
FIG. 3 is a schematic of an example of hydrogel formation using a maleimide-functionalized low molecular weight heparin (LMWH) and a thiol-functionalized (thiolated) four-arm polyethylene glycol (PEG)

Hydrogel Formation Analysis by $^1$H NMR:

Auto-oxidation of thiols is well known to occur in solution, and could possibly occur prior to or during hydrogel formation. Hydrogelation was monitored via $^1$H-NMR to confirm the extent at which any disulfide bond formation occurred during gelation. The Michael-type addition of the thiol to the maleimide for gelation (as illustrated in FIG. 3) was verified using $^1$H-NMR of hydrogels formed in deuterated buffers. Gelation experiments were conducted by loading 60 ul of thiol-functionalized PEG, maleimide-functionalized LMWH, or mixtures of both into a single opening 1.5-1.8×90 mm borosilicate glass capillary. The filled capillary was placed in a standard NMR tube containing 700 μl of the deuterated buffer. Measurements (32 scans, room temperature) were taken under standard acquisition parameters for both MP and MPP functionalized PEG at 10, 30, 60 minutes, and 2 and 8 hrs. The spectra in FIG. 5 show complete disappearance of the maleimide protons (6.82 and 6.8 ppm) as well as the protons from the mercaptoacid moieties (centered at 2.7 ppm for MP, and 2.6, 2.8, 7.0 and 7.2 ppm for MPP) without the appearance of new peaks for disulfide bond or ring-opened maleimides.

Rates of disulfide bond formation under these conditions were also determined via standard Ellman's assay. These data illustrate that the rate of disulfide formation occurred the fastest for aryl thiol-functionalized PEG, with an oxidation half-life of 13.5 hrs., and the slowest for alkyl thiol-functionalized PEG with an oxidation half-life of 4.7 days. The rate of disulfide bond formation was significantly slower than the rate of maleimide-thiol reactions, as expected, under these conditions.

Hydrogel Degradation Analysis by $^1$H NMR:

The hydrolysis or retro-Michael-type additions for degradation (as illustrated in FIG. 4) were verified using $^1$H-NMR of hydrogels formed in deuterated buffers. Degradation experiments to verify reduction sensitivity were completed on MPP-functionalized PEG-LMWH hydrogels. A 60 ul hydrogel was formed (using deuterated PBS lacking GSH for the gelation) in the bottom of a standard NMR tube (below the receiver coils of the NMR). The degradation of PEG-MPP-containing PEG-LMWH hydrogels was monitored via $^1$H-NMR to verify the mechanism of degradation under reducing environments. The liberation of small molecules into the buffer above the hydrogel was monitored in the NMR experiment. The degradation experiments were conducted on gels that were swelled at 37° C. (using deuterated PBS containing 10 mM glutathione at pH 7.4), with measurements taken at every 24 hrs. To increase the sensitivity of the spectral runs, an increased acquisition time of 8.2 s was used.

It has been previously reported for small-molecule model compounds that the succinimide thioether products of the addition of aromatic thiols to maleimides are susceptible to thiol exchange in reducing environments where exogenous thiols are present; indeed, 4-mercaptophenylacetic acid-maleimide adducts were shown to cleave up to 85% after 70 hrs.

FIG. 6 shows the results of the experiment; the spectra of the starting hydrogel to soluble macromers are shown (traces A-D) with a magnified view showing the position of the aromatic protons (6.7 ppm to 7.6 ppm), which were sensitive to the chemical substituents of the thiol and thus provided a facile metric for confirming the mechanism of degradation. Trace A shows the starting MPP-LMWH hydrogel (from NMR experiments of gelation), with clear broadening of the aromatic protons owing to the conjugation of the thiol with the maleimide. Trace D shows unreacted and soluble PEG-MPP for comparison. The amount of soluble PEG-MPP above the degrading hydrogel was not significant until the hydrogel was no longer visibly distinguishable from the solution; trace B shows the clear appearance of the protons from the free PEG-MPP at day 3. At this point there is a mixture of PEG-MPP conjugated to LMWH, as indicated by the presence of both the broad peaks centered at 7.2 and 7.4 ppm, and the PEG-MPP aromatic protons centered at 6.9 and 7.2 ppm. The slight shift in the position of the aromatic protons from the positions in the gelation studies above (i.e. 6.9 versus 7.0 ppm) is most likely due to slight differences in the solution pH values between the experiments. Trace C displays the NMR spectrum at day 4; at this time point most of the succinimide thioether linkages have degraded, yielding mainly the soluble PEG-MPP. Hydrogels incubated in the absence of GSH did not show the appearance of the peaks from the soluble PEG-MPP (data not shown).

Hydrogel Degradation Analysis by Oscillatory Rheology:

The reduction in modulus as a function of degradation was monitored by oscillatory rheology by swelling the perimeter of the hydrogel with standard or reducing buffers. Hydrogels were formed as described above with slight modification to the procedure. Before adding the solutions to the Peltier plate, a polyvinylchloride (PVC) ring with a height of 7 mm, inside diameter of 35 mm and an outside diameter of 42 mm was pre-coated with a thin film of silicone vacuum grease on the bottom and positioned above the geometry by a ring stand and clamp. After the crosslinked hydrogel had reached equilibrium the rheometer bearing was locked to prevent disruption of the hydrogel while the mineral oil was washed away three times with hexane. The PVC tube was then firmly pressed onto the Peltier plate creating a water-tight seal with the vacuum grease. The volume between the gel and cylinder walls was filled with 2 ml of buffer (50 mM phosphate, 150 mM NaCl, 10 mM or 10 µM GSH at pH 7.4) and topped with mineral oil to prevent evaporation. A buffer concentration of 50 mM (versus 10 mM as described above) with was used to maintain a constant pH throughout the experiment. Data points were collected every 5 minutes over 5 days.

Oscillatory rheology experiments provided a means to assess both the kinetics of degradation of the hydrogels as well as the changes in mechanical properties that occur with degradation. For comparison, the extended degradation timescales of the maleimide-thiol crosslinked hydrogels were compared with PEG-SH hydrogels cross-linked by disulfide linkages. The control disulfide hydrogel was composed of 5.3 wt % four-arm thiolated PEG with a storage modulus of 3 kPa. The formation of the control hydrogel required approximately 24 hrs. to form an equilibrated hydrogel even when using the Fenton-type catalyst as previously described. Degradation of the gels was monitored in the presence of GSH-containing buffer via direct measurement of the modulus using oscillatory rheology. The hydrogels were constricted between the rheometer geometry and Peltier plate, whereby the swelling of the hydrogel was prevented axially. Radial swelling was negligible; therefore, the reduction in storage moduli was directly related to the scission of active crosslinks absent of swelling effects. Furthermore, a bath volume of 2 ml (50 excess of hydrogel) provided an adequate sink so that pH and reductant concentration were unaffected during the experiment.

The PEG-SH hydrogels rapidly degraded when exposed to high concentrations of reductant, with a near-zero modulus observed in 4 hours. As shown in FIGS. 7A and 7B, PEG-MPP- and PEG-DMMPP-containing hydrogels show much lower susceptibility to the GSH, consistent with the fact that the rate constants for the retro Michael-type addition are an order of magnitude lower than those for glutathione-disulfide exchange. The sensitivity to GSH is maintained over 72 hours, indicated by the increased rate of degradation observed upon exchange of the surrounding buffer with 10 mM GSH at this time point. The fact that this degradation rate is slightly slower than that for when the hydrogels are initially immersed in 10 mM GSH buffer is consistent with the ring opening of the succinimide, which renders the gels less sensitive to GSH.

The degradation profiles were evaluated via standard rubber elasticity theory assuming that the rate of scission of any network active chain correlates with a reduction in modulus; a slight modification in the value of f was made to account for the less defined maleimide functionality of the LMWH. The complicated kinetics of the retro Michael-type addition produced an overall non-first order degradation curve. As degradation proceeds, the amount of available succinimide thioethers diminishes, resulting in an apparent reduction in the degradation rate. This trend is then followed by an accelerated degradation as the hydrogel enters the depercolation regime. Thus, the pseudo-first order kinetics of the retro reaction can only be approximated under the initial timescales when a majority of the succinimide rings are intact and susceptible to thiol exchange via the retro Michael-type addition. Given that the half-life of succinimide thioether rings for similar small molecules were reported to be on the order of 200 hrs, the first 15 hours were fit to exponential decay equations to minimize the impact of the ring opening on the retro-Michael-type addition constants.

The determined rate constants were $0.039 \pm 0.006$ hr$^{-1}$ for PEG-MPP and $0.031 \pm 0.003$ hr$^{-1}$ for PEG-DMMPP containing PEG-LMWH hydrogels. Given the linearity of the degradation curve for the PEG-SH gels, these rate constants were estimated by fitting the entire curve, yielding pseudo-first order constants of $0.81 \pm 0.1$ hr$^{-1}$. These pseudo-first order rates are consistent with typical values (5 to 0.9 hr$^{-1}$) for disulfide mediated cleavage, and previously derived succinimide thioether retro Michael adducts comprising aryl thiol substituents (0.0371 hr$^{-1}$). The agreement of the rate constants determined from the degradation experiments with those previously reported for small-molecule model studies suggests that the diffusion of glutathione to the center of the 20-mm rheometer geometry (calculated to require 10 hours (based on an approximated diffusion coefficient for glutathione of $6 \times 10^{-6}$ cm$^2$/s) does not introduce significant non-uniformity in the degradation to complicate our analysis. Notably, complete degradation of the PEG-SH hydrogel occurs within 4 hours, suggesting that diffusion of glutathione may be accelerated by the degradation of the hydrogel network as well as an increase in molecular motion provided by the oscillatory straining of the hydrogel.

Hydrogel Degradation Measured by Heparin Release:

The increased stability of the succinimide-thioether bond, relative to the disulfide bond, provides opportunities to utilize these chemistries for a more sustained release of drugs under the high reducing loads present in intracellular compartments and tumor microenvironments. The release of LMWH from the hydrogels was thus investigated. 40 µL hydrogels were formed in a 0.5 ml tuberculin syringe with the tip removed using the same mixing method described above. The resulting hydrogels had a diameter of 3.5 mm and a length of 4 mm. The truncated syringe was sealed with Parafilm® to minimize evaporation during gelation. Cast gels were incubated at 37° C. for the length of time, indicated by oscillatory rheology experiments, required for the storage modulus to reach a plateau. Gels were then ejected by advancing the syringe plunger. Released gels were incubated in a bath of 4 ml buffer at 37° C. Highly reducing conditions in vivo were mimicked by using 10 mM phosphate buffer with 150 mM sodium chloride and 10 mM GSH at pH 7.4. Standard reducing conditions were mimicked using lower concentrations of GSH (10 µM). 1 ml samples were taken and replenished with fresh buffer at time points of 0, 1, 6, 12, and 24 hrs initially, then every 12 hrs for 2 days, every 24 hrs for 4 additional days, every 48 hrs for 4 additional days, every 72 hrs for 18 additional days, and every 96 hrs. for the remaining 23 days.

The concentration of heparin in solution was measured using established toluidine blue measurements with slight modification. 100 ul of collected sample were mixed with 800 ul toluidine blue solution (0.005% toluidine blue in 50 mM HCl) and 100 ul dichloromethane in 1.5 ml centrifuge tubes. The solutions were mixed and incubated overnight at room temperature followed by centrifugation at 20,000×g for 20 minutes. The absorbance of the aqueous phase was measured using an Agilent 8453 spectrophotometer (Santa Clara, Calif., USA) in a Hellma 3 mm quartz cuvette (Plainview, N.Y., USA). Absorbance maxima at 590 and 632 nm were recorded. Calibration curves were constructed using functionalized LMWH. No difference in calibration was noted when stock solution of functionalized LMWH was reacted with thiolated PEGs or small molecule thiols.

FIG. 8 shows the release of LMWH, for all hydrogels, under standard reducing conditions in blood circulation (10 µm GSH, open symbols) compared to that under the high reductant load commensurate with intracellular compartments and tumor microenvironments (10 mM GSH, solid symbols). All materials showed some burst release of LMWH within the first day (~23%), likely due to the large polydispersity of LMWH and potentially poor efficiency of crosslinking. The average functionalization of the LMWH is approximately 2.6; therefore, a small amount of low molecular weight species (roughly 3% from GPC data) are without maleimide functionality and free to diffuse from the hydrogel. Hydrogels were also formed in dilute solutions (5 wt %), as discussed above, and exhibited low crosslinking efficiencies; consequently, the formation of loops and intramolecular crosslinks enable free or partially reacted but non-crosslinked LMWH to be released within the first day.

The hydrogels containing the GSH-sensitive succinimide thioether linkages (PEG-MPP and PEG-DMMPP) release 100% LMWH over 12 and 20 days under standard reducing conditions, while they rapidly degrade under the high reducing conditions, completely releasing LMWH within 3 and 4 days (FIGS. 8A and 8B, respectively). Comparatively, the release profiles for the hydrogels containing GSH-insensitive linkages (PEG-MP and PEG-MIB) show significantly less sensitivity to reducing conditions, requiring 20 and 49 days for PEG-MP and PEG-MIB under standard reducing conditions and 17 and 33 days under high reductant load. This slight increase in LMWH release rate for the PEG-MP and PEG-MIB gels was not expected, given the lack of retro Michael-type reactions observed in our previous studies even when glutathione was present in 100× excess over the succinimide thioether substituent. The sensitivity of the gels to a 1:1 stoichiometry of GSH in this hydrogel experimental format may suggest that GSH transesterification is promoted by the relatively high concentration of thiolate (0.1 mM) over hydroxyl groups (0.3 uM) in the gel.

The acceleration in LMWH release for the PEG-MP and PEG-MIB gels at the later time points in the experiments may be due to a depercolation transition in the hydrogels as degradation proceeds. The absence of this defined point in the PEG-MPP and PEG-DMMPP gels, particularly under standard reducing conditions, suggests that some process resulting in a reduction in degradation rate competes with this depercolation. This is likely due to the ring opening of the succinimide, which eliminates their capacity for the retro Michael-type addition and thiol exchange, as we have previously demonstrated.

What is claimed is:

1. A composition comprising a bioactive molecule and a second component, wherein the bioactive molecule and the second component are linked by one or more linking units comprising a thioether structural unit having the structural formula -A-S—R— where A is an aryl moiety or a heteroaromatic ring moiety and R is a succinimide moiety and obtained by Michael-type addition of a thiol to a maleimide group and wherein the thiol has a pKa of less than 8, and wherein the composition is capable of undergoing a retro Michael-type addition reaction under physiological conditions.

2. The composition of claim 1, wherein the linking units have the structural formula —$R^5$—$R^1$—S—R—$R^2$-$R^3$— where R is a succinimide moiety, $R^1$ and $R^2$ are each independently a C2-C16 organic moiety and $R^3$ and $R^5$ are each independently a functional group covalently bound to the bioactive molecule or the second component, with R being covalently bound to $R^2$ through a nitrogen atom of the succinimide moiety, S being covalently bound to R through a carbon atom of the succinimide moiety, and $R^1$ having an aryl moiety, a heteroatomic ring moiety, or a carbonyl-substituted alkyl group covalently bound to S.

3. The composition of claim 2, wherein $R^3$ and $R^5$ are independently selected from the group consisting of amino, amido, ester, ether, alkenyl, triazole, urethane, urea and thio functional groups.

4. The composition of claim 1, wherein the thiol has a pKa of less than 7.

5. The composition of claim 2, wherein $R^1$ is selected from the group consisting of —$CH_2$—$CH_2$—$C_6H_4$—, —$C(CH_3)_2$—$CH_2$—$C_6H_4$—, and —$CH_2$—$C_6H_4$—, the —$C_6H_4$— moiety being covalently bound to S.

6. The composition of claim 1, wherein the thiol is an aryl thiol or a heteroaromatic ring-containing thiol.

7. The composition of claim 1, wherein the second component is a polymer.

8. The composition of claim 7, wherein the polymer is at least one hydrophilic polymer selected from the group consisting of polyalkylene glycols, poly(vinyl alcohols), poly(acrylamides), poly(acrylic acids), poly(methacrylic acids), poly(hydroxyalkylacrylates), poly(hydroxyalkylmethacrylates), heparins, gelatins, collagens, alginates and hyaluronic acids.

9. The composition of claim 8, wherein the hydrophilic polymer has a number average molecular weight of 1000 to 20,000 g mol$^{-1}$.

10. The composition of claim 8 wherein the hydrophilic polymer is polyethylene glycol.

11. The composition of claim 1, wherein the bioactive molecule is selected from the group consisting of polysaccharides, growth factors, cytokines, peptides, polymers covalently modified with peptides, proteins, polymers covalently modified with polysaccharides, peptoids, polymers covalently modified with peptoids, and small-molecule drugs.

12. The composition of claim 1, wherein the bioactive molecule is a polysaccharide.

13. The composition of claim 12, wherein the polysaccharide is a low molecular weight heparin (LMWH).

14. The composition of claim 1, where the composition is a hydrogel.

15. The composition of claim 1, wherein the composition is water-soluble.

16. A method of delivering a bioactive molecule to a site within a subject where one or more endogenous or exogenous thiols are present, said method comprising administering to the subject a composition in accordance with claim 1, wherein the composition undergoes a retro Michael-type addition reaction to regenerate the thiol and the maleimide group rendering the bioactive molecule permanently liberated from the composition after reaction of the endogenous or exogenous thiols with the maleimide group at the site, whereby the bioactive molecule provides a therapeutic effect to the subject upon release.

17. A composition comprising a bioactive molecule and a polymer, wherein the polymer comprises a plurality of segments linked by one or more linking units comprising a thioether structural unit having the structural formula -A-S—R— where A is an aryl moiety or a heteroaromatic ring moiety and R is a succinimide moiety and obtained by Michael-type addition of a thiol to a maleimide group and wherein the thiol has a pKa of less than 8, and wherein the composition is capable of undergoing a retro Michael-type addition reaction under physiological conditions.

* * * * *